United States Patent
Beauvais et al.

(10) Patent No.: US 8,943,897 B2
(45) Date of Patent: Feb. 3, 2015

(54) CARBON NANOTUBES BASED SENSING ELEMENTS AND SYSTEM FOR MONITORING AND MAPPING FORCE, STRAIN AND STRESS

(75) Inventors: Jacques Beauvais, Sherbrooke (CA); Patrick Boissy, Sherbrooke (CA); Jonathan Genest, Sherbrooke (CA); Annick Sauve, Bromont (CA)

(73) Assignee: Societe de Commercialisation des Produits de la Recherche Appliquee—Socpra-Sciences et Genie S.E.C., Sherbrooke, Quebec (CA)

( * ) Notice: Subject to any disclaimer, the term of this patent is extended or adjusted under 35 U.S.C. 154(b) by 180 days.

(21) Appl. No.: 13/519,409

(22) PCT Filed: Dec. 29, 2010

(86) PCT No.: PCT/CA2010/002071
§ 371 (c)(1),
(2), (4) Date: Oct. 1, 2012

(87) PCT Pub. No.: WO2011/079390
PCT Pub. Date: Jul. 7, 2011

(65) Prior Publication Data
US 2013/0031987 A1    Feb. 7, 2013

Related U.S. Application Data

(60) Provisional application No. 61/291,183, filed on Dec. 30, 2009.

(51) Int. Cl.
*G01B 7/16* (2006.01)
*A61B 5/11* (2006.01)
(Continued)

(52) U.S. Cl.
CPC ............ *A61B 5/1126* (2013.01); *A61B 5/1038* (2013.01); *A61B 5/447* (2013.01); *A61B 5/6846* (2013.01); *B82Y 15/00* (2013.01); *G01B 7/18* (2013.01); *G01L 1/18* (2013.01); *G01L 1/205* (2013.01); *G01L 1/2293* (2013.01); *A61B 2562/0285* (2013.01)
USPC .............................................. 73/777; 73/774

(58) Field of Classification Search
CPC ... G01N 27/127; Y10S 977/742; B82Y 35/00
USPC .......................................... 73/760, 774, 777
See application file for complete search history.

(56) References Cited

U.S. PATENT DOCUMENTS

| 6,936,653 | B2 * | 8/2005 | McElrath et al. | ............. 524/496 |
| 7,129,467 | B2 * | 10/2006 | Wincheski et al. | ........ 250/214.1 |

(Continued)

FOREIGN PATENT DOCUMENTS

| GB | 2 427 756 B | 7/2009 |
| WO | WO 2007/001315 A2 | 1/2007 |

*Primary Examiner* — Max Noori
(74) *Attorney, Agent, or Firm* — Muirhead and Saturnelli, LLC

(57) ABSTRACT

The present disclosure relates to an element for sensing strain, stress or force. The sensing element comprises a substrate, a pair of electrodes on the substrate, and a network of carbon nanotubes for sensing the strain, stress or force within a structure. The network of carbon nanotubes defines at least in part an electrical path between the electrodes of the pair, and the electrical path has a resistance which is altered by the sensed strain, stress or force. Combining a plurality of sensing elements coupled to a common substrate forms a sensing system.

20 Claims, 12 Drawing Sheets

(51) Int. Cl.
    *A61B 5/103*    (2006.01)
    *A61B 5/00*     (2006.01)
    *B82Y 15/00*    (2011.01)
    *G01L 1/18*     (2006.01)
    *G01L 1/20*     (2006.01)
    *G01L 1/22*     (2006.01)

(56) References Cited

U.S. PATENT DOCUMENTS

| | | | |
|---|---|---|---|
| 7,194,912 B2 * | 3/2007 | Jordan et al. | 73/774 |
| 7,278,324 B2 * | 10/2007 | Smits et al. | 73/799 |
| 7,439,731 B2 * | 10/2008 | Crafts et al. | 324/756.03 |
| 7,593,004 B2 | 9/2009 | Spath et al. | |
| 7,730,547 B2 * | 6/2010 | Barrera et al. | 850/21 |
| 7,973,305 B2 * | 7/2011 | Jiang et al. | 257/24 |
| 7,990,161 B2 * | 8/2011 | Ju et al. | 324/698 |
| 8,338,897 B2 * | 12/2012 | Kim et al. | 257/417 |
| 8,399,279 B2 * | 3/2013 | Lim et al. | 438/52 |
| 2003/0087130 A1 * | 5/2003 | Sugawara | 428/692 |
| 2004/0043527 A1 * | 3/2004 | Bradley et al. | 438/48 |
| 2006/0253942 A1 | 11/2006 | Barrera et al. | |
| 2007/0222472 A1 | 9/2007 | Raravikar et al. | |
| 2008/0034842 A1 * | 2/2008 | Lee et al. | 73/31.05 |
| 2008/0251723 A1 * | 10/2008 | Ward et al. | 250/338.4 |
| 2009/0153512 A1 * | 6/2009 | Jiang et al. | 345/173 |

* cited by examiner

CARBON NANOTUBES BASED SENSING ELEMENTS AND SYSTEM FOR MONITORING AND MAPPING FORCE, STRAIN AND STRESS

RELATED APPLICATIONS

This application claims priority to U.S. Provisional App. No. 61/291,183, field Dec. 30, 2009.

TECHNICAL FIELD

The present disclosure relates to the field of sensing devices. More specifically, the present disclosure relates to a sensing element comprising a network of carbon nanotubes and to a sensing system comprising such sensing element(s).

BACKGROUND

A network of carbon nanotubes exhibits piezoresistive properties sensitive to mechanical strain, stress and/or force. Pressure applied to carbon nanotubes, for example by a probe, affects their electronic properties at a nanoscale. When disposed in networks, carbon nanotubes may be used to sense strain, stress and deformation at a macroscale. Consequently, carbon nanotubes have been used for making sensing devices.

Although such sensing devices have demonstrated their usefulness in monitoring of changes inside structures, there has been a continuing need for improvement, especially for distinguishing the nature of a deformation and for mapping a deformation over time.

SUMMARY

According to a first aspect, there is provided a sensing element comprising a substrate, a pair of electrodes on the substrate, and a multidimensional network of carbon nanotubes coupled to the electrodes and applied to the substrate between the electrodes.

According to a second aspect, there is provided a sensing element comprising a substrate, first and second electrodes coupled to the substrate, a mobile structure, a first network of carbon nanotubes extending between the first electrode and the mobile structure, and a second network of carbon nanotubes extending between the second electrode and the mobile structure. The first and second networks are interconnected at the mobile structure so that the first and second networks of carbon nanotubes define at least partially an electrical path between the first and second electrodes.

According to a third aspect, there is provided a sensing element comprising a substrate, a pair of electrodes on the substrate, and a multidimensional network of carbon nanotubes for sensing strain, stress or force within a structure. The network of carbon nanotubes defines at least in part an electrical path between the electrodes of said pair. The electrical path has a resistance which is altered by the sensed strain, stress or force.

The foregoing and other features will become more apparent upon reading of the following non-restrictive description of illustrative embodiments thereof, given by way of example only with reference to the accompanying drawings.

BRIEF DESCRIPTION OF THE DRAWINGS

In the appended drawings:

FIG. 108 is a schematic side elevation view of the sensing element for multidimensional strain measurement of FIG. 10A;

DETAILED DESCRIPTION

Figure 1:
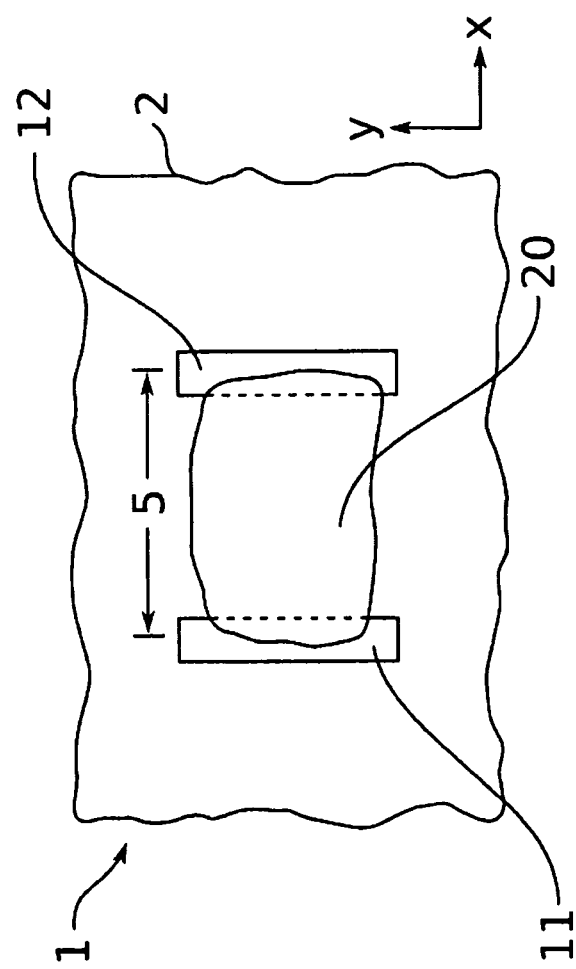
FIG. 1 is a schematic top plan view of an example of sensing element comprising a network of carbon nanotubes.

Disclosed in the following description is a sensing element using the piezoresistive properties of a network of carbon nanotubes positioned between two electrodes. To measure mechanical strain, stress and/or force, the network of carbon nanotubes is positioned in an area where it may be stretched and/or compressed. This may be achieved, for example, by:

Moving the two electrodes with respect to one another to stretch and/or compress the network of carbon nanotubes;

Stretching and/or compressing the network of carbon nanotubes modifying an electric path between the two electrodes; or Compressing the network of carbon nanotubes perpendicular to a plane in which the electrodes are lying, for example through a layer of compliant material; or Bending the substrate in a region defined by the two electrodes to stretch and/or compress the network of carbon nanotubes.

The carbon nanotubes are connected together forming a multidimensional mesh in order to obtain a network of conduction paths. The conduction paths formed inside the carbon nanotube network are used to measure the variation of the electric resistance of the carbon nanotube network caused by its elongation or contraction following the application of an external force.

A network of carbon nanotubes exhibits intrinsic piezoresistive properties, both because of an intrinsic piezoresistive nature of the individual carbon nanotubes and of percolative properties of electronic transport in a network of carbon nanotubes. An electronic percolation model may be used to express the variation of electrical resistance in the network of carbon nanotubes, and a direct correlation may be established between a variation of electrical resistance of a network of carbon nanotubes and the mechanical strain and stress sustained by that network of carbon nanotubes. If this strain results from the application of an external force, a direct correlation may be established between the calculated strain, the sensing element geometry and the external force.

If a sensing element based on a network of carbon nanotubes sustains mechanical strain, local deformations in the network of carbon nanotubes induce changes in the resistance of the sensing element. More specifically, a resistance R of the network of carbon nanotubes is altered. A relative resistance ($R/R_0$) may be calculated according to equation (1):

$$\frac{R}{R_0} = \frac{s}{s_0} \exp[-\gamma(s_0 - s)] \quad (1)$$

where:
$R_0$ is an original or "reference" resistance in the absence of externally generated strain;
$s_0$ is an original or "reference" mean distance between carbon nanotubes inside the network in the absence of externally generated strain;
s is a mean distance between carbon nanotubes resulting from the mechanical strain, stress and/or force; and
y is a constant that depends on a height of an electrical potential barrier between adjacent nanotubes.

If stress is applied to the network of carbon nanotubes, the mean distance s between the carbon nanotubes changes. In the case of uniaxial stress σ, the mean distance s may be expressed according to equation (2):

$$s = s_0(1 - \varepsilon) = s_0\left(1 - \frac{\sigma}{E}\right) \quad (2)$$

where:
$\varepsilon$ is the sustained strain; and
E is an elastic modulus of the network of carbon nanotubes.

The elastic modulus of the network of carbon nanotubes is mostly defined by material filling a space between the carbon nanotubes. This filling material may be a gas, a liquid or a solid. In a valid electronic percolation model, the Young's modulus of the filling material is smaller than a Young's modulus of the individual carbon nanotubes. In fact, carbon nanotubes have a Young's modulus at least five times larger than that of steel.

A substrate for receiving a network of carbon nanotubes in a sensing element may be made from a variety of materials such as silicon, glass, polymers, metals or a combination of the preceding and/or other materials. A function of the substrate is to support a sensing element based on a network of carbon nanotubes or a sensing system comprising such sensing element(s), for example an assembly of such sensing elements. The substrate may also be used to limit a number of degrees of freedom of a sensing element or sensing system.

Metallic materials such as copper, aluminum, silver, gold or chromium, or metallic alloys may be used to build electrodes in a sensing element. Such metallic materials have high conductivity and high mechanical stiffness and demonstrate good electrical coupling with the network of carbon nanotubes. Other conductive material such as semiconductors, conductive polymers or carbon nanotubes may also be employed.

A mechanically compliant layer for covering the network of carbon nanotubes in a sensing element may be made from a huge variety of materials such as rubber, silicon rubber, acrylic, polydimethylsiloxane (PDMS), polyethylene terephthalate (PET), epoxy, electrically insulated metals, etc. A main function of the mechanically compliant layer is to act as a linear spring that deforms itself in direct proportion to a stress applied. A strain versus stress relationship of the compliant layer material is known and used to calculate the resulting stress applied to the sensing element. The external force applied to the sensing element and causing the stress and strain sustained by the sensing element may be calculated from the measured strain, the elastic modulus of the compliant material and the cross section of the compliant layer. Depending on this strain versus stress relationship, different ranges of forces and stresses may be measured by the sensing element. The compliant layer also acts as a protector for the network of carbon nanotubes and for the electrodes, preventing degradation of their properties. The compliant layer may also be patterned to alter its friction coefficient or sticking properties. The compliant layer may further be reinforced in order to enable the sensing element to sustain a high level of force and/or stress. It is possible to cap the compliant layer with a material demonstrating a higher resistance to wear and abrasion.

A sensing element based on a network of carbon nanotubes may be used to sense and monitor strain, stress and/or force on a variety of structures. Potential structures for coupling or embedding sensing elements include prosthesis, rehabilitation equipment, artificial skin, textile, and numerous other applications.

Figure 2A:
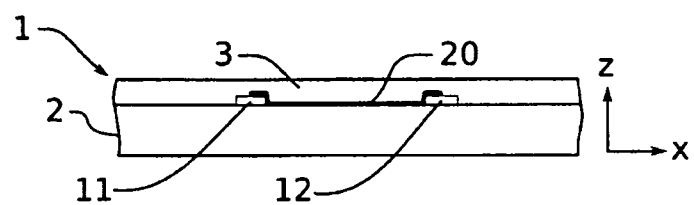
FIG. 2A is a schematic side elevation view of the sensing element of FIG. 1, capped with a layer of compliant material.

FIG. 1 is a schematic top plan view of an example of sensing element including a network of carbon nanotubes. FIG. 2A is a schematic side elevation view of the sensing element of FIG. 1, capped with a compliant layer. Referring to both FIGS. 1 and 2A, the sensing element 1 for sensing strain, stress and/or force comprises a substrate 2 and a set of spaced apart electrodes 11 and 12 mechanically coupled to a face of the substrate 2 and separated by a gap 5. A network 20 of carbon nanotubes, including for example non-aligned, partially aligned, roughly aligned or randomly aligned carbon nanotubes, is applied to and may be mechanically coupled and to the face of the substrate 2. The network 20 of carbon nanotubes is also electrically and mechanically coupled to the two (2) spaced-apart, opposed electrodes 11 and 12 to act as a strain, stress and/or force sensitive area. As illustrated, a portion of the network of carbon nanotubes spans on top of each electrode 11, 12 of the sensing element 1. The carbon nanotubes may be single-wall and/or multi-wall carbon nanotubes. A mechanically compliant layer 3 may cover at least the network 20 of carbon nanotubes and may further cover a part or whole of the electrodes 11, 12 and the substrate 2. As shown, the electrodes 11 and 12 are parallel and facing each other. This arrangement is shown for illustration purposes and not for purposes of limitation. In practice, various arrangements of the electrodes 11 and 12 may be conceived, wherein electrodes are not parallel and not facing each other. In an embodiment, two electrodes may be linked, for example by an L-shape or a U-shape network of carbon nanotubes. Later figures of the present disclosure will show alternate embodiments. The sensing element 1 comprises the network 20 of carbon nanotubes that are non-aligned, partially aligned, roughly aligned or randomly aligned. Carbon nanotubes within the network 20 actually occupy a two-dimensional (2D) space between the electrodes and may occupy a three-dimensional (3D) space between the electrodes when the network of carbon nanotubes has a non-negligible thickness along the z axis of FIG. 2A. Because at least a fraction of the carbon nanotubes are not aligned in a straight path between the electrodes 11 and 12, the sensing element 1 is capable of measuring a magnitude of strain, stress and/or force over two or three dimensions.

Figure 2B:
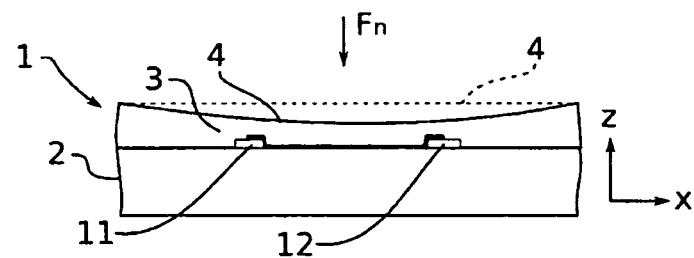
FIG. 2B is a schematic side elevation view of the sensing element of FIG. 1, capped with a layer of compliant material to which a force is applied.

FIG. 2B is a second schematic side elevation view of the sensing element of FIG. 1. If the substrate 2 is made of rigid material, the configuration of FIGS. 1, 2A and 2B may be used to measure normal strain, stress and force. More specifically, as a normal force $F_n$ is applied to a top surface 4 of the compliant layer 3, the compliant layer 3 distorts and compresses in the direction of the applied force $F_n$, compressing the network 20 of carbon nanotubes under it. When the network 20 of carbon nanotubes is compressed, a mean distance between carbon nanotubes decreases and a relative resistance $R/R_0$ of the network 20 of carbon nanotubes decreases exponentially with the strain being sustained.

As shown on FIG. 2B, the normal force $F_n$ is applied in a direction of the z axis, perpendicular to the x-y plane. In an embodiment, the substrate 2 and the compliant layer 3 may be made of stretchable materials. This configuration may be employed to measure tensile strain, stress and/or force along a direction parallel to the axis x passing through both electrodes 11 and 12. For example, the substrate 2 may be mechanically coupled to a structure (not shown) to detect and monitor strain, stress and/or force in that structure. In this configuration, stretching the structure on which the sensing element 1 is coupled increases the mean distance between the carbon nanotubes of the network 20 along the axis x, increasing the relative resistance $R/R_0$ (equation (1)). In yet another embodiment, using a narrow width of the network 20 of carbon nanotubes in the direction y perpendicular to the axis x passing through both electrodes 11 and 12, minimizes the influence of stretching in this direction y on the measurement. Alternatively, significant length and width of the network 20, along the x and y axes respectively, allows measuring a force applied at any angle within the x-y plane. The sensing element 1 may further detect an applied tangential force having components along all x, y and z axes.

Figure 3:
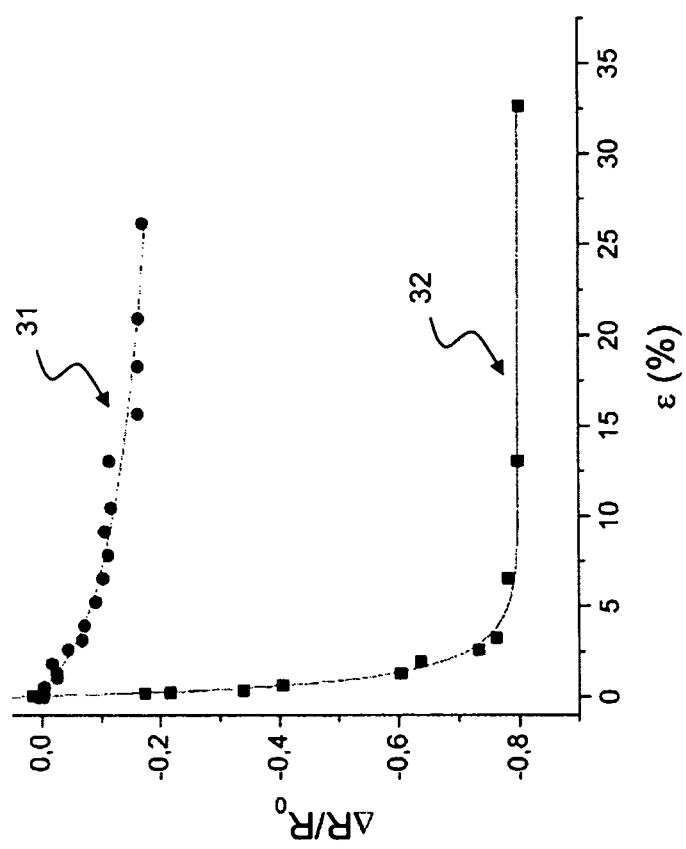
FIG. 3 is a graph showing relations between electric resistances of two nanotube networks as a function of compressive strain.

FIG. 3 is a graph showing relations between electric resistances of two nanotube networks as a function of compressive strain. The relations are expressed as a resistance variation $\Delta R/R_0$, on a vertical axis, as a function of a compression value $\epsilon$, expressed as a percentage on a vertical axis, for networks of carbon nanotubes with two (2) distinct compositions. In a first case (round dots 31), the network of nanotube is made from a self-supported film of purified single-wall carbon nanotubes (SWNT) grown by induction thermal plasma. This film is made of a densely woven mesh of high purity (~99%) single-wall carbon nanotubes bundles. In the case of the purified film, the resistance variation and compressive strain may be expressed as $\Delta R/R_0 \propto \exp(-12.0\epsilon)$. In the second case (square dots 32), the network of nanotube is made from a self-supported film fabricated in situ directly in a carbon nanotube growth reactor. This film contains loosely woven bundles of carbon nanotubes with non-tubular impurities. The carbon nanotubes appear to be uniformly distributed among the impurities. The concentration of carbon nanotubes in the film fabricated in situ is ~40%, the rest of the material being composed of metallic catalysts and carbon black. In the case of the film fabricated in situ, the relation between the resistance variation and compressive strain may be expressed as $\Delta R/R_0 \propto \exp(-120.7\epsilon)$.

Figure 4:
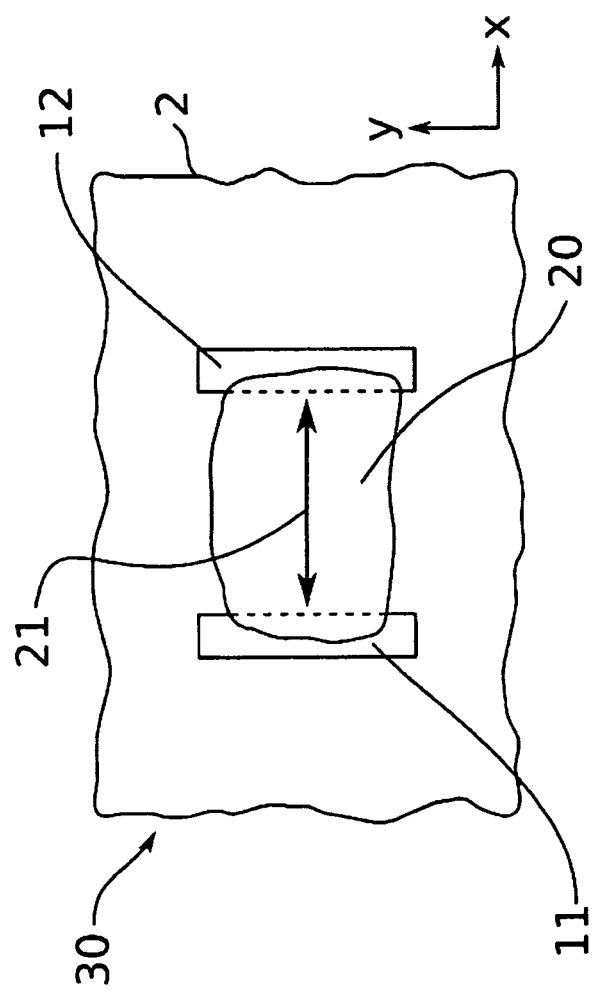
FIG. 4 is a schematic top plan view of an example of sensing element comprising a network of at least partially aligned carbon nanotubes.

In a further embodiment, the strain measurement is isolated to a single direction 21 by electrically coupling the electrodes 11 and 12 with a network of carbon nanotubes composed of carbon nanotubes that are at least partially or roughly aligned in the direction of the axis x passing through both electrodes 11 and 12. FIG. 4 is a schematic top plan view of an example of sensing element showing a network of aligned carbon nanotubes. According to this embodiment, the carbon nanotubes in the network 20 are aligned by mean of, for example, molecular forces, shear forces, electrophoresis, dielectrophoresis, magnetic forces, or any other suitable process. The carbon nanotubes composing the sensing area of the network 20 are then perpendicular to the electrodes 11 and 12. Alternatively, the carbon nanotubes may be aligned parallel to the electrodes 11 and 12, or at any angle thereto.

The configurations shown in FIG. 1, 2A, 2B or 4, coupled to a bendable but unstretchable substrate, may be employed to detect and monitor bending. The relative resistance $R/R_0$ changes with the angle of bending of the substrate. More specifically, the relative resistance $R/R_0$ decreases for concave bending while increasing for convex bending.

For that purpose, the sensing element 1 may be built starting from a bendable substrate 2 such as, for example, a Kapton® film. The electrodes 11 and 12 may be made of conductive epoxy deposited on the substrate 2 by screen printing and then cured in an oven. A drop of carbon nanotubes suspension is then deposited in the gap 5 between the electrodes 11 and 12. After the solvent has evaporated, the sensing element 11 is immersed in a bath of alcohol to dissolve surfactant from the suspension of carbon nanotubes. The sensing element 1 is then dried and encapsulated with a thin, mechanically compliant layer of flexible polymer such as PDMS. Alternatively, a self-supported membrane containing at least one carbon nanotube network may be glued to the substrate and electrically coupled to the electrodes, for example with conductive epoxy.

Figure 5:
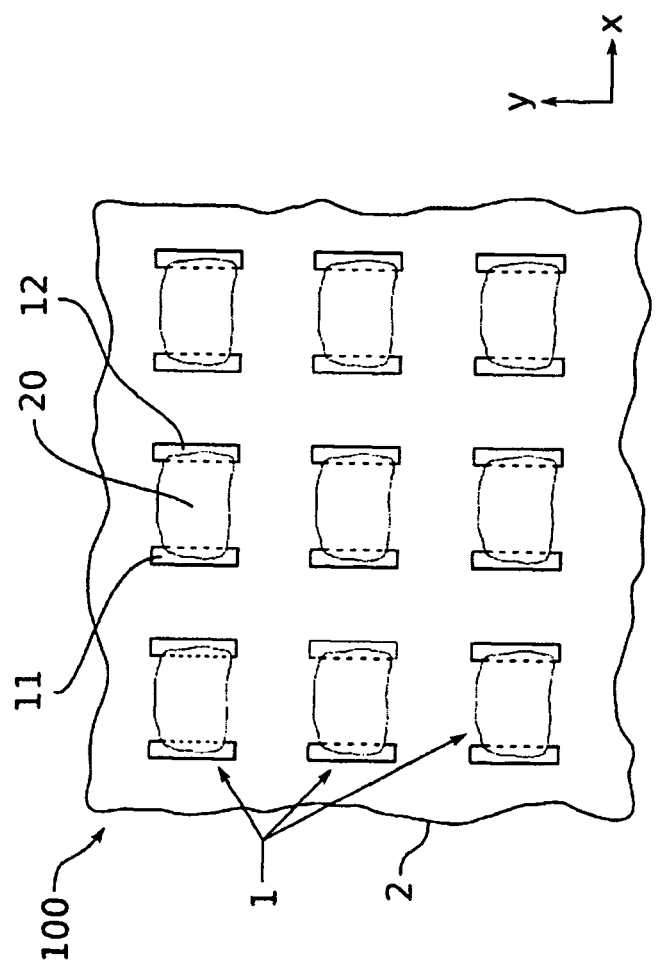
FIG. 5 is a schematic top plan view of an example of sensing system comprising a single level array of sensing elements.

FIG. 5 is a schematic top plan view of an example of sensing system comprising a single level array of multiple sensing elements. In the array 100 of the sensing system, a plurality of sensing elements 1 are disposed and mechanically coupled to a substrate 2. FIG. 5 shows, for exemplary purpose and not by way of limitation, nine (9) sensing elements 1. Of course, smaller or larger numbers of sensing elements 1 may be used to form the array of multiple sensing elements 1, as a function of the requirements of the intended application. The substrate 2 may in turn be mechanically coupled to a structure (not shown) to detect and monitor strain, stress and/or force in that structure. The sensing elements 1 of FIG. 5 may be disposed in various geometries and in any desired position, according to any desired pattern, and may have any desired size adequate to form, for example, a sensing system for sensing, monitoring and mapping different components of strain, stress and/or force over a given surface of the structure. More specifically, depending on a chosen disposition of the sensing elements 1, it is possible to determine strain components in six (6) different directions, comprising strain components along any one of axes x, y or z ($\epsilon_{xx}$, $\epsilon_{yy}$, $\epsilon_{zz}$) or in any plane defined by two of the axes x, y and z ($\epsilon_{xy}$, $\epsilon_{xz}$, $\epsilon_{yz}$). From the known mechanical properties (strain versus stress relationship) of the compliant material of, for example, layer 3 and the known geometry of the sensing elements 1, six (6) stress components along the same axes and planes ($\sigma_{xx}$, $\sigma_{yy}$, $\sigma_{zz}$, $T_{xy}$, $T_{xz}$, $T_{yz}$) and three (3) force components along the same axes and planes ($F_x$, $F_y$, $F_z$) may also be calculated if at least six (6) sensing elements are used non-collinearly. To determine the strain, stress and force components, piezoresistive properties of the sensing elements 1 are multiplexed and monitored when the structure and the networks 20 of carbon nanotubes coupled thereto are experiencing a deformation. The resistance variation of the sensing elements 1 may be multiplexed and monitored continuously over time.

In an embodiment, for the purpose of facilitating calculation, the sensing elements 1 of FIG. 5 may be disposed uniformly and have identical sizes. The sensing elements 1 may be capped with a layer of compliant material which provides a contact surface for the application of a force. In a further embodiment, the layer of compliant material may be patterned in an array of plows located directly on top of each sensing element 1 to reduce lateral crosstalk by producing discontinuities in the compliant material.

Figure 6:
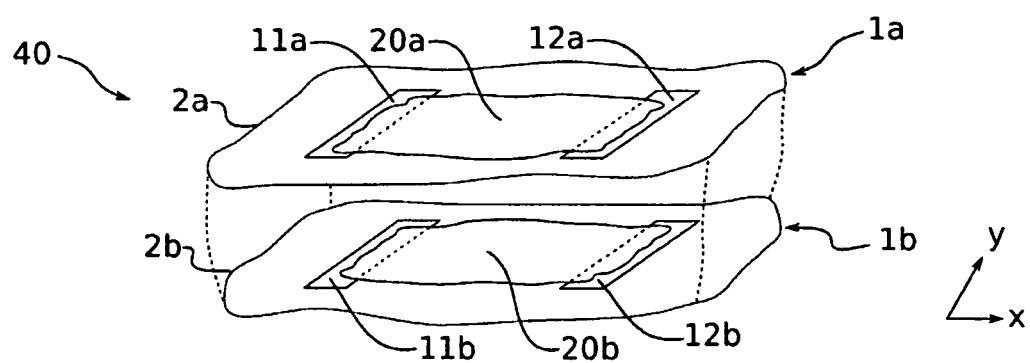
FIG. 6 is a perspective view of an example of sensing system comprising an assembly of superposed sensing elements including respective networks of carbon nanotubes.

An example sensing system 40 comprising multi-level multiple sensing elements is illustrated in FIG. 6. The sensing system 40 comprises at least two (2) sensing elements 1a and 1b disposed on top of each other and separated from each other by an intermediate compliant layer (not shown). The two (2) sensing elements 1a and 1b may each be similar to the above described sensing element 1. The sensing element 1a comprises a substrate 2a, a pair of electrodes 11a and 12a, and a network 20a of carbon nanotubes. The sensing element 1b comprises a substrate 2b, a pair of electrodes 11b and 12b, and a network 20b of carbon nanotubes. In addition to compressive and tensile strain, in this configuration, the sensing elements 1a and 1b may be used to measure shear strain by capacitive measurement. A simple electronic switch (not shown) may be employed to measure alternatively compressive/tensile and shear strain. In yet another embodiment, adding additional level(s) to the sensing system 40 may be used to increase shear strain sensitivity.

Figure 7:
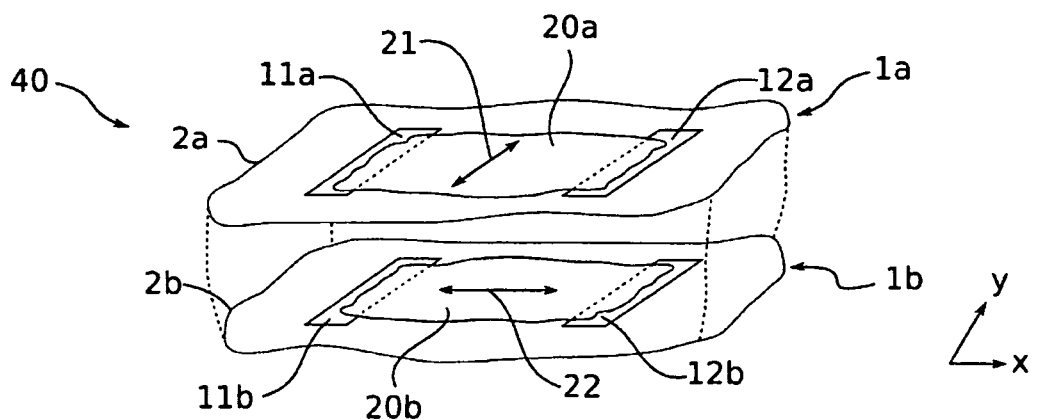
FIG. 7 is a perspective view of another example of sensing system comprising an assembly of superposed sensing elements including respective networks of at least partially aligned carbon nanotubes.

FIG. 7 is a perspective view of another example of sensing system comprising a plurality of sensing elements with respective networks of at least partially aligned carbon nanotubes. The configuration depicted in FIG. 7 is similar to that of FIG. 6. In this example, within the two (2) sensing elements 1a and 1b, the networks 20a and 20b comprises carbon nanotubes at least partially aligned in perpendicular directions 21 and 22, respectively. As illustrated in FIG. 7, the sensing elements 1a and 1b are positioned on top of each other and separated by a layer (not shown) of compliant material in order to isolate contributions to the tensile strain along the axes x and y.

Figure 8:
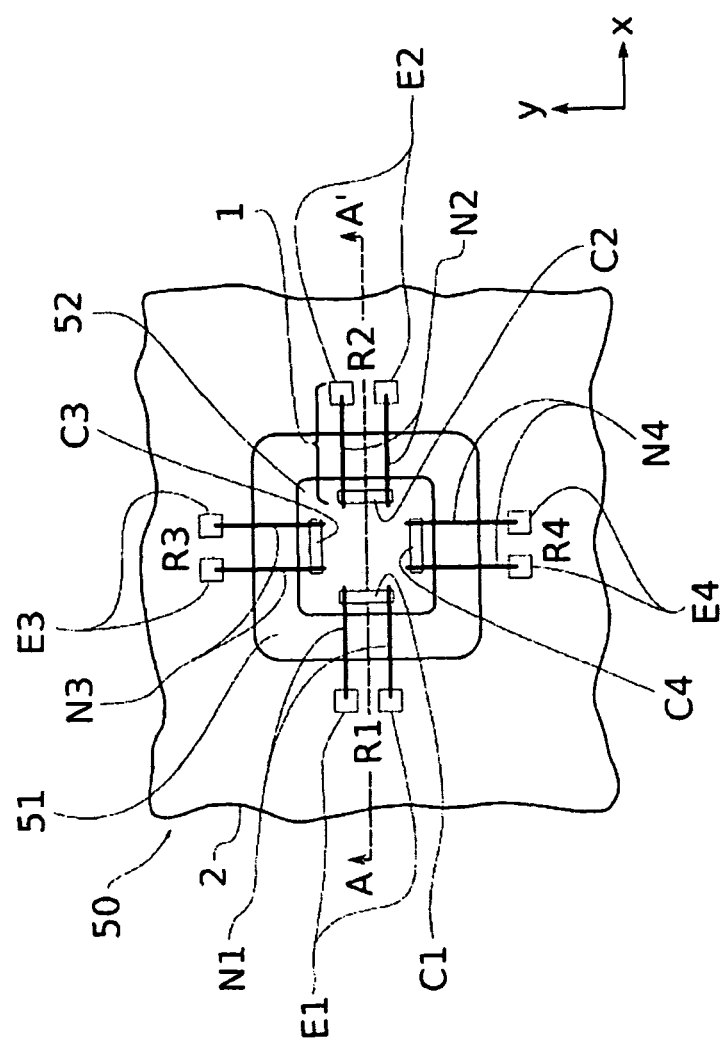
FIG. 8 is a schematic top plan view of an example of sensing element for triaxial strain measurement.

Another exemplary embodiment as illustrated in FIG. 8 is a triaxial sensing element 50 for triaxial strain measurement. The triaxial sensing element 50 comprises a mobile structure 52 located laterally and vertically offset from a set of pairs of electrodes E1, E2, E3 and E4 positioned non-collinearly and mechanically coupled to one face of the substrate 2. The mobile structure 52 may be embedded in a layer 51 of compliant material, for example an elastomer layer, which extends at least partially between the mobile structure 52 and the pairs of electrodes E1, E2, E3 and E4. The pairs of electrodes E1, E2, E3 and E4 are electrically linked to the mobile structure 52 through a set of independent pairs of networks N1, N2, N3 and N4 of carbon nanotubes, which are positioned at least partially on the compliant layer 51 or embedded at least partially therein. Each independent pair of networks N1, N2, N3 or N4 of carbon nanotubes includes a respective electrically conductive member C1, C2, C3 or C4 on the mobile structure 52 to define a continuous electrical path between the corresponding pair of proximally located electrodes E1, E2, E3 or E4. Sensing elements having similar features as those of the sensing element 1 of FIG. 1 are formed on the substrate 2, comprising for example the pair of electrodes E2, the corresponding pair of networks N2 of carbon nanotubes and the corresponding conductive member C2. Triaxial strain measurement is then conducted through measurement of variations in resistance R1, R2, R3 and R4 of the continuous electrical paths between the corresponding pairs of proximally located electrodes E1, E2, E3 and E4, respectively including (a) one pair of networks N1, N2, N3 or N4 of carbon nanotubes and (b) the corresponding conductive member C1, C2, C3 or C4.

The following other implementations are possible. For example, considering the pair of electrodes E1 and the corresponding pair of networks N1 of carbon nanotubes forming with the respective conductive member C1 an electrical path having a resistance R1, an alternative embodiment could comprise a U-shaped network of carbon nanotubes connected at its respective ends to the electrodes E1; in this implementation, the conductive member C1 may be omitted. In yet another alternative implementation, one electrode E1 of the corresponding pair may be located on a fixed part, such as the substrate 2, of the sensing element 50, while the other electrode E1 may be located on the mobile structure 52. Various other implementations of a network of carbon nanotubes having a sufficient length, between two electrodes, for providing an electrical path capable of reacting to strain, stress and/or force in the sensing element of FIG. 8 may be envisioned. The above implementations apply to the other pairs of electrodes E2, E3 and E4, pairs of networks N2, N3 and N4 of carbon nanotubes, and conductive members C2, C3 and C4.

Figure 9A:
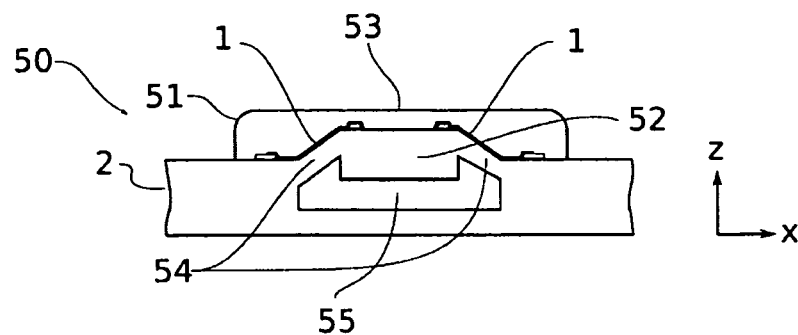
FIG. 9A is a schematic side elevation view of the sensing element of FIG. 8.
Figure 9B:
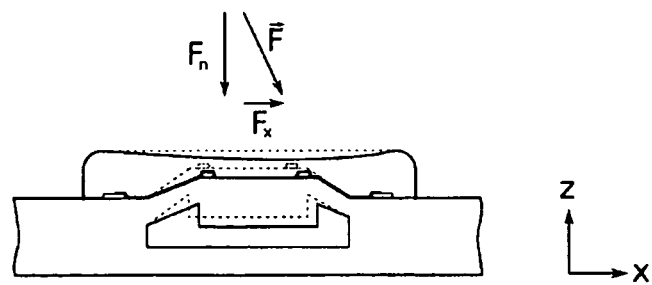
FIG. 9B is a schematic side elevation view of the sensing element of FIG. 8, to which a force is applied.

FIGS. 9A and 9B are schematic side elevation views of the sensing element of FIG. 8. If a force F composed of a normal component $F_n$ and a shear component $F_x$ is applied to a top face 53 of the compliant capping layer 51, above the mobile structure 52, a compliant layer 54 is deformed and the mobile structure 52 is moved vertically and horizontally with respect to its original position. The material of this compliant layer 54 may be identical or different from the material of the capping layer 51. A volume 55 under the mobile structure 52 may be empty or filled with a compliant material, which also may be identical or different from the material of the capping layer 51. On FIG. 9B, dotted lines show the original position of the mobile structure 52 and solid lines show its position after movement thereof. The resulting position of the mobile structure 52 is measured by piezoresistivity of the pairs of networks N1, N2, N3 and N4 of carbon nanotubes. More specifically, the piezoresistivity provides a measurement of a variation of a resistance of the pairs of networks N1, N2, N3 and N4 of carbon nanotubes between the respective pairs of electrodes E1, E2, E3 and E4. A distance between the set of pairs of electrodes E1, E2, E3 and E4 and the mobile structure 52 may be calculated from the measured resistances and a known piezoresistivity relation. Since a plurality of piezoresistive sensing elements 1 are disposed around the mobile structure 52, displacement of the mobile structure 52 results in different resistance variations from the different networks of carbon nanotubes from which strain may be calculated. With an unstretchable substrate, three (3) pairs of networks of carbon nanotubes, disposed non-collinearly may be used to determine three (3) of the six (6) strain tensor components ($\epsilon_{zz}$, $\epsilon_{xz}$, $\epsilon_{yz}$). As illustrated in FIG. 8, four (4) pairs of networks of carbon nanotubes may be used to simplify calculations.

Figure 10A:
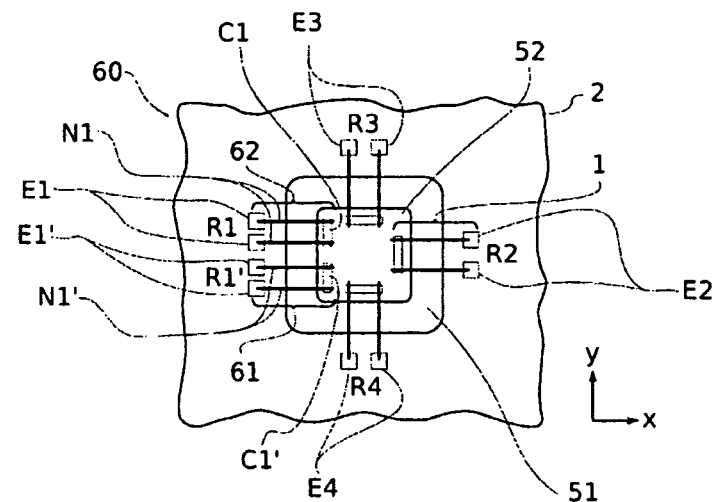
FIG. 10A is a schematic top plan view of another example of sensing element for multidimensional strain measurement.
Figure 10B:
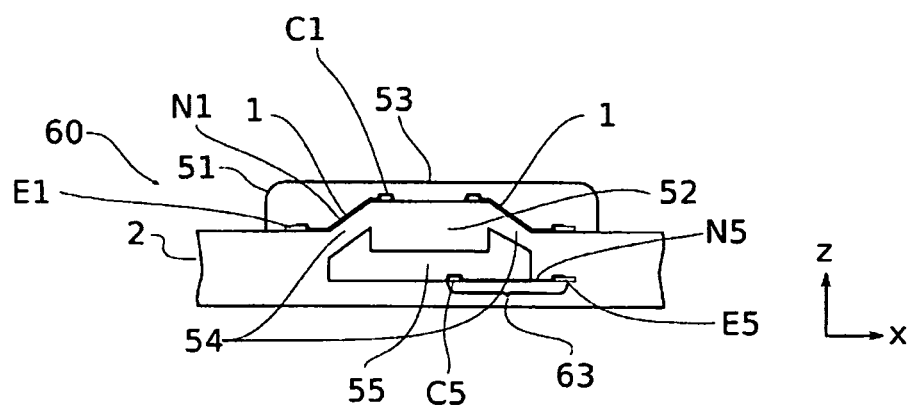

FIGS. 10A and 10B are a schematic top plan view and a schematic side elevation view, respectively, of another example of triaxial sensing element 60 for multidimensional strain measurement. The triaxial sensing element 60 is similar to the triaxial sensing element 50 of FIG. 8, in which a second electrode assembly 61 is added on one side next to an electrode assembly 62 including the pair of electrodes E1, the pair of networks N1 of carbon nanotubes and the conductive member C1 completing the conductive path between the electrodes E1. The electrode assembly 61 comprises a pair of electrodes E1', a pair of networks N1' of carbon nanotubes and a conductive member C1' completing the conductive path between the electrodes E1'. Two others electrode assemblies 63, are added and disposed non-collinearly in the x-y plan, one of which is illustrated on FIG. 10b. Using the sensing element 60, the whole strain tensor ($\epsilon_{xx}$, $\epsilon_{yy}$, $\epsilon_{zz}$, $\epsilon_{xy}$, $\epsilon_{xz}$, $\epsilon_{yz}$) may be determined. As described hereinabove, stress and force components may also be calculated using the known mechanical properties of the compliant material of layer 51. At least six (6) pairs of networks of carbon nanotubes may be used to determine all six (6) strain tensor components and, then, the stress and force components may be calculated from the mechanical properties of the compliant material and the strain tensor components.

Referring both to FIGS. 8 and 10A, components of the strain tensor may be determined from the relative resistances R1, R1', R2, R3 and R4 measured between the pairs of electrodes E1, E1', E2, E3 and E4. A mean of the relative resistances R1 and R1', is calculated according to equation (3):

$$R1_{mean} = \frac{R1 + R1'}{2} \tag{3}$$

Strain tensor components along the axes x, y and z ($\epsilon_{xx}$, $\epsilon_{yy}$, $\epsilon_{zz}$) or within the planes defined by two of the axes x, y and z ($\epsilon_{xy}$, $\epsilon_{xz}$, $\epsilon_{yz}$) are calculated according to equations (4 to 9):

$$\varepsilon_{xx} = f\left(R5 - \frac{R1_{mean} + R2}{2}\right) \tag{4}$$

$$\varepsilon_{yy} = f\left(R6 - \frac{R3 + R4}{2}\right) \tag{5}$$

$$\varepsilon_{zz} = f\left(\frac{R1_{mean} + R2 + R3 + R4}{4} - \frac{R5 + R6}{2}\right) \tag{6}$$

$$\varepsilon_{xz} = \varepsilon_{zx} = f(R1_{mean} - R2) \tag{7}$$

$$\varepsilon_{yz} = \varepsilon_{zy} = f(R3 - R4) \tag{8}$$

$$\varepsilon_{xy} = \varepsilon_{yx} = f(R1 - R1') \tag{9}$$

In equations (4) to (9), $f$ designates a function of the direct correlation between the variation of the electric resistance of the network of carbon nanotubes and the strain sustained by that network. It may be observed from equation (9) that the strain $\epsilon_{xy}$ is determined as a function of a difference between R1 and R1'.

Figure 11:
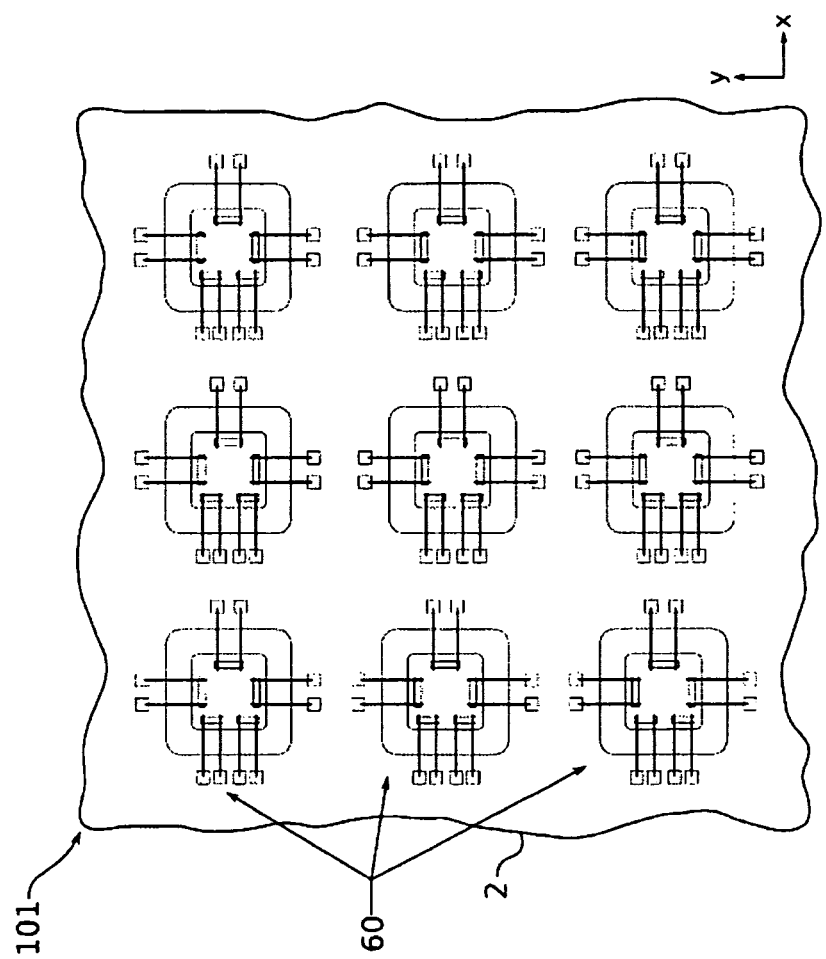
FIG. 11 is a schematic top elevation view of a sensing system comprising an array of sensing elements as illustrated in FIG. 10.

As illustrated in FIG. 11, a plurality of sensing elements 60 may be arranged in an array 101 to form a sensing device that may be used to map strain distribution over a surface. In this implementation, the top face 53 (FIG. 8A) of the layer 51 of compliant material of each sensing element 60 is coupled to the surface of which strain distribution is mapped.

Figure 12:
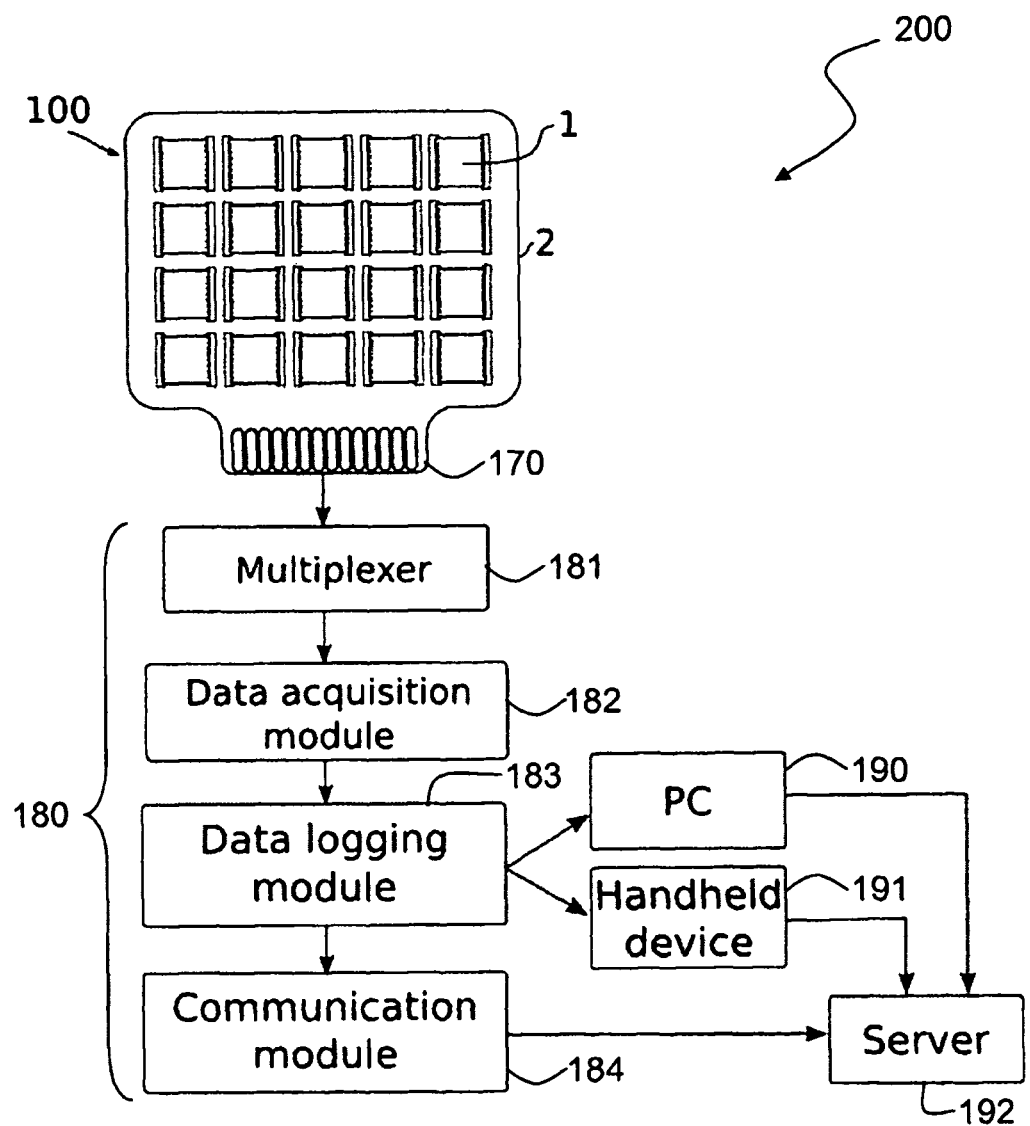
FIG. 12 is a block diagram illustrating an example of a strain/stress/force monitoring system.

FIG. 12 is a block diagram illustrating an example a strain/stress/force monitoring system. As illustrated in FIG. 12, an array 100 of FIG. 5 is combined with an electronic circuitry 180 and with a processing unit to complete a sensing system 200. Of course, a sensing system may also be built using any of the sensors described in relation to any of the preceding figures. Therefore, FIG. 12 illustrates an embodiment including the array 100 without suggesting limitation and solely for illustration purposes. As shown, the electronic circuitry 180 is adapted to connect to the array 100 via a connector 170 of the array 100. The electronic circuitry 180 may probe and electronically compare the electrical properties of each sensing element of the array 100, for example by connecting via the connector 170 to the electrodes such as 11 and 12 of the sensing element 1 or such as the electrode pairs E1, E1', E2, E3 and E4 of the sensing element 50 or 60 within the array 101 of FIG. 11. A multiplexer 181 may sample data from the array 100 or 101 and transmit the data through a data acquisition module 182 to a data logging module 183 and further to a processing unit such as a personal computer (PC) 190, a handheld device 191 and further to a server 192, either through the PC 190 or handheld device 191 or through a communication module 184. In various embodiments, at least parts of the electronic circuitry 180 may be located within the sensing element or may be remotely located.

Figure 13:
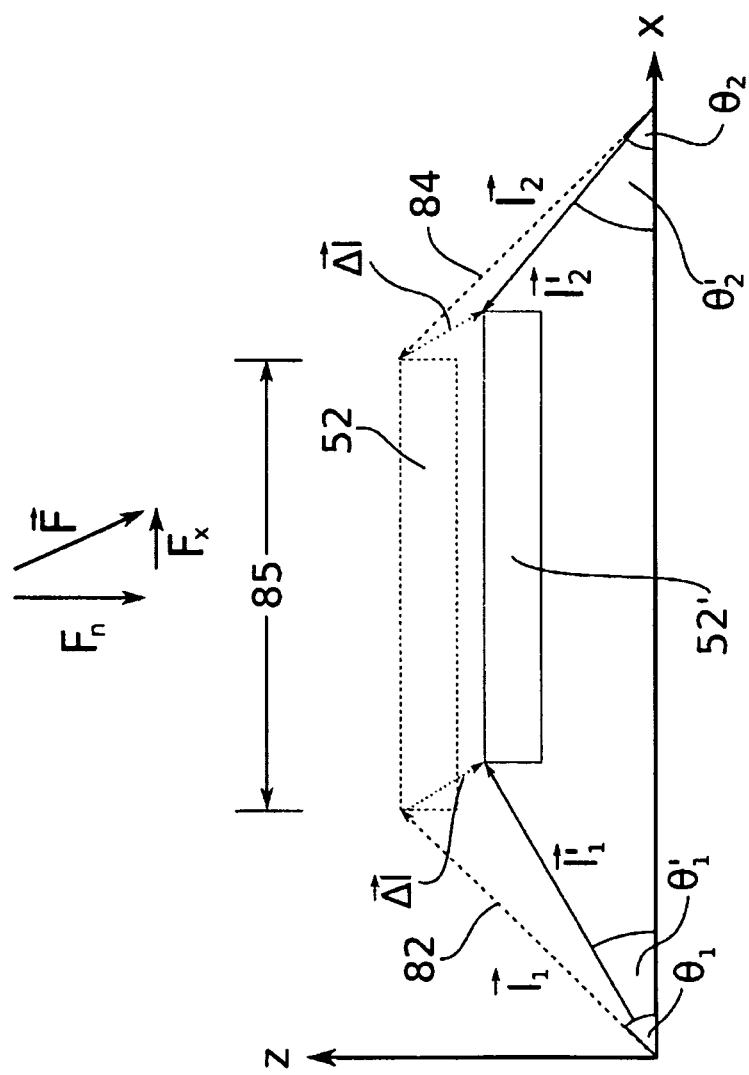
FIG. 13 is a simplified schematic side elevation view of a sensing element as illustrated in FIG. 10.

FIG. 13 is a simplified schematic side elevation view of a sensing element 60 as illustrated in FIG. 10. Using FIG. 13, an example of strain calculation method will be described in a simplified, two-dimensional (2D) illustration (in the plane x-z) of movements within the sensing element 60. FIG. 13 is not to scale and does not represent actual relative sizes of its various elements. FIG. 13 is presented in schematic form for illustration purposes. Equations for calculating the whole strain tensor may be extrapolated from following 2D equations. The mobile structure 52 sustains an applied force F composed of a normal component $F_n$ and a shear component $F_x$. Networks of carbon nanotubes are positioned on each side 82 and 84 of the mobile structure 52, linking the mobile structure 52 to the substrate 2 (shown on earlier Figures). In this particular case, for illustration purposes, the substrate 2 is made of unstretchable material and the mobile structure 52 is designed to prevent rotation of the mobile structure 52 in the x-z plane or to minimize its effect on the whole displacement of the mobile structure 52. This may be achieved by choosing the width 85 of the mobile structure 52 such that it is very small compare to the lengths $l_1$ and $l_2$ of the networks of carbon nanotubes or by designing the capping layer 53 in order that the force F is centered on the mobile structure 52. In a non-limiting embodiment, the mobile structure 52 is positioned so that lengths $l_1$ and $l_2$ of the networks of carbon nanotubes are equal at equilibrium, according to the relation of equation (10):

$$|l_1| = |l_2| = |l| \tag{10}$$

Under the force F, an initial position of the mobile structure 52, shown in dotted lines, changes following a vector defined in equation (11):

$$\overline{\Delta l} = \Delta x \hat{i} + \Delta z \hat{k} \tag{11}$$

where $\Delta x \hat{i}$ represents the component of the displacement of the mobile structure 52 along the axis x and $\Delta z \hat{k}$ represents the component of the displacement of the mobile structure 52 along the axis z.

The mobile structure 52 reaches a position under strain, shown in solid lines at 52'. On each side 82, 84 of the mobile structure 52, the networks of carbon nanotubes are stretched or compressed to new lengths, according to equations (12) and (13):

$$|l_1'| = |l|(1+\epsilon_1) \tag{12}$$

$$|l_2'| = |l|(1+\epsilon_2) \tag{13}$$

where $\epsilon_1$ and $\epsilon_2$ represent a linear strain sustained by the networks of carbon nanotubes. It may be observed that the values $\epsilon_1$ and $\epsilon_2$ may be negative, as in the case of $\epsilon_2$ in relation to FIG. 13.

Initially, the angles $\theta_1$ and $\theta_2$ may be equal. As the linear strain is applied to the mobile structure, the angles are slightly modified and become $\theta_1'$ and $\theta_2'$ as shown on FIG. 13. In practice, the angles are only very slightly altered and their variation may be neglected in the following equations.

Since the networks of carbon nanotubes are calibrated, the linear strain for each network of carbon nanotubes may be determined from its relative resistance $R/R_0$, following equations 1 and 2, thus $|l_1'|$ and $|l_2'|$ are known, $\overline{\Delta l}$ may be calculated according to equations (11), (14) and (16):

$$|l_1'|^2 - |l_2'|^2 = 4|l||\Delta x|\cos\theta_1 \quad (14)$$

$$|\Delta x| = \frac{|l_1'|^2 - |l_2'|^2}{4|l|\cos\theta_1}$$

From the above, equations (15) and (16) may be derived:

$$|l_1'|^2 + |l_2'|^2 = 2(|l|^2 + |l||\Delta z|\sin\theta_1 + |\Delta l|^2) \quad (15)$$

$$\frac{|l_1'|^2 + |l_2'|^2}{2} - |l|^2 - |\Delta x|^2 = |l||\Delta z|\sin\theta_1 + |\Delta z|^2$$

$$\frac{|l_1'|^2 + |l_2'|^2}{2} - |l|^2 - |\Delta x|^2 = \left(|\Delta z| + \frac{|l|\sin\theta_1}{2}\right)^2 - \frac{|l|^2\sin^2\theta_1}{4}$$

$$\left(|\Delta z| + \frac{|l|\sin\theta_1}{2}\right)^2 = \frac{2|l_1'|^2 + 2|l_2'|^2 + |l|^2(\sin^2\theta_1 - 4) - 4|\Delta x|^2}{4}$$

$$|\Delta z| = \sqrt{\frac{2|l_1'|^2 + 2|l_2'|^2 + |l|^2(\sin^2\theta_1 - 4) - 4|\Delta x|^2}{4}} - \frac{|l|\sin\theta_1}{2}. \quad (16)$$

By assuming that $|\Delta l|^2 \ll |l|$, equation (15) may then be expressed according to equation (17):

$$\frac{|l_1'|^2 + |l_2'|^2}{|l|} = 2\left(\frac{|l|^2}{|l|} + \frac{|l|}{|l|}|\Delta z|\sin\theta_1 + \frac{|\Delta l|^2}{|l|}\right) \quad (17)$$

$$\frac{|l_1'|^2 + |l_2'|^2}{|l|} \approx 2(|l| + |\Delta z|\sin\theta_1)$$

$$|\Delta z| \approx \frac{|l_1'|^2 + |l_2'|^2 - 2|l|^2}{2|l|\sin\theta_1}$$

Equation (14) calculates the movement of the mobile structure 80 along the axis x and equation (17) calculates the movement of the mobile structure along the axis z. From the above, the strain components may be estimated as:

$$\varepsilon_{zz} = \frac{\Delta z}{|l_1|\sin\theta_1} \quad (18)$$

$$\varepsilon_{xz} = \frac{\Delta x}{|l_1|\sin\theta_1} \quad (19)$$

From simple geometrical considerations, those of ordinary skill in the art will be able to extrapolate the above equations for calculating the whole strain tensor.

The sensing elements disclosed hereinabove may be used, for instance, for monitoring the stress applied on a body part, such as the sole of a foot or an injured limb under a prosthesis. For people with specific conditions that increase exposure to compressive and shear forces, it may be desirable to monitor stress sustained over specific body areas to prevent tissue ulceration due to accumulated compressive and shear stress. This may be the case, for example, for bed ridden individuals, for people with an inability to move certain parts of their body without assistance, such as after spinal or brain injury or as a consequence of neuromuscular disease, and for people having a chronic condition that prevents areas of the body from receiving proper blood flow, as in the case of diabetic patients. Using sensors system disclosed herein, a real-time mapping and monitoring of stress applied on a body part is achievable and may lead to novel therapeutic approaches for preventing the development of pressure ulcers.

The sensing elements disclosed herein may also be used, not only for biofeedback application, but also for monitoring and mapping the stress over the surface of an arbitrary object, such as the exterior surface of a wheel, to monitor its traction on the ground, or a robot prehensile tool, in order to control the applied force needed to manipulate an object without damaging it or letting it slip.

Although the present disclosure has described non-restrictive illustrative embodiments of the sensing element and sensing system, these embodiments can be modified at will within the scope of the appended claims without departing from the spirit and nature of the present disclosure.

What is claimed is:

1. A sensing system, comprising:
   at least two sensing elements disposed on top of each other, each sensing element including:
   a substrate;
   a pair of electrodes on the substrate; and
   a multidimensional network of carbon nanotubes coupled to the electrodes and applied to the substrate between the electrodes,
   wherein the carbon nanotubes in the network of one of the at least two sensing elements are at least partially aligned in a first direction and the carbon nanotubes in the network of the other of the at least two sensing elements are at least partially aligned in a second direction,
   wherein the multidimensional network of carbon nanotubes of one or more of the at least two sensing elements is configured for sensing strain, stress or force within the one or more of the at least two sensing elements, and
   wherein the network of carbon nanotubes of the one or more of the at least two sensing elements defines at least in part an electrical path between the electrodes of the one or more of the at least two sensing elements, the electrical path having a resistance which is altered by the sensed strain, stress or force.

2. A sensing system as defined in claim 1, wherein at least one of the at least two sensing elements comprises a mechanically compliant layer covering the network of carbon nanotubes.

3. A sensing system as defined in claim 1, wherein the substrate of one or more of the at least two sensing elements is made of stretchable material.

4. A sensing system as defined in claim 2, wherein the substrate and the mechanically compliant layer of one or more of the at least two sensing elements are made of stretchable material.

5. A sensing system as defined in claim 1, wherein the substrate of the one or more of the at least two sensing elements is mechanically coupled to a structure to detect and monitor strain, stress or force within the structure.

6. A sensing system as defined in claim 1, wherein the substrate of the one or more of the at least two sensing elements is a bendable but non stretchable substrate for allowing the sensing element to detect and monitor bending.

7. A sensing system as defined in claim 1, comprising a plurality of sensing elements arranged into an array on a common substrate.

8. A sensing system as defined in claim 7, wherein the common substrate is mechanically coupled to a structure to detect and monitor strain, stress or force in that structure.

9. A sensing system as defined in claim 7, wherein the sensing elements of the array are capped with a layer of compliant material.

10. A sensing system as defined in claim 9, wherein the layer of mechanically compliant material is patterned.

11. A sensing system as defined in claim 1, wherein the at least two sensing elements are separated by a compliant layer.

12. A sensing system as defined in claim 1, wherein one or more of the at least two sensing elements comprises a two-dimensional network of carbon nanotubes.

13. A sensing system as defined in claim 1, wherein one or more of the at least two sensing elements comprises a three-dimensional network of carbon nanotubes.

14. A sensing element comprising:
a substrate;
first and second electrodes coupled to the substrate;
a mobile structure;
a first network of carbon nanotubes extending between the first electrode and the mobile structure; and
a second network of carbon nanotubes extending between the second electrode and the mobile structure, the first and second networks being interconnected at the mobile structure, the first and second networks of carbon nanotubes defining at least partially an electrical path between the first and second electrodes,
wherein the mobile structure is offset from the first and second electrodes,
wherein at least one of the first and second networks of carbon nanotubes is configured for sensing strain, stress or force within the at least one of the first and second networks of carbon nanotubes; and
wherein the electrical path has a resistance which is altered by the sensed strain, stress or force.

15. A sensing element as defined in claim 14, comprising an electrically conductive member on the mobile structure for interconnecting the first and second networks of carbon nanotubes.

16. A sensing element as defined in claim 14, wherein the mobile structure is embedded in a layer compliant material which extends at least partially between the mobile structure and the first and second electrodes.

17. A sensing element as defined in claim 16, wherein the first and second networks of carbon nanotubes are positioned at least partially on the layer of compliant material.

18. A sensing element as defined in claim 16, wherein the first and second networks of carbon nanotubes are embedded at least partially in the compliant layer.

19. A sensing element, comprising:
a substrate;
first and second electrodes coupled to the substrate;
a mobile structure, wherein the mobile structure is offset from the first and second electrodes;
a first network of carbon nanotubes extending between the first electrode and the mobile structure;
a second network of carbon nanotubes extending between the second electrode and the mobile structure, the first and second networks being interconnected at the mobile structure; and
a plurality of non-collinear assemblies each including:
said first and second electrodes coupled to the substrate; and
said first network of carbon nanotubes extending between the first electrode and the mobile structure, and the second network of carbon nanotubes extending between the second electrode and the mobile structure, the first and second networks being interconnected at the mobile structure whereby the first and second networks of carbon nanotubes define at least partially an electrical path between the first and second electrodes.

20. A sensing system comprising a plurality of sensing elements as defined in claim 14, wherein the plurality of sensing elements comprise a common substrate and are arranged into an array on the common substrate.

* * * * *